(12) United States Patent
Rieger (10) Patent No.: US 6,716,185 B1
(45) Date of Patent: Apr. 6, 2004

(54) WRIST ANGLE BRACE

(76) Inventor: Christopher L. Rieger, 24643 Red Robin Dr., Bonita Springs, FL (US) 34135

( * ) Notice: Subject to any disclaimer, the term of this patent is extended or adjusted under 35 U.S.C. 154(b) by 0 days.

(21) Appl. No.: 10/272,359

(22) Filed: Oct. 15, 2002

(51) Int. Cl.[7] ................................................. A61F 5/00
(52) U.S. Cl. ........................ 602/21; 128/879; 2/161.1
(58) Field of Search ................................ 602/20, 5, 21, 602/22, 64, 62, 61, 60, 19; 2/18–21, 16; 473/62, 61, 213, 212; 482/46, 45; 128/879

(56) References Cited

U.S. PATENT DOCUMENTS

| | | | |
|---|---|---|---|
| 1,469,315 A | | 10/1923 | Hansard |
| 3,423,095 A | | 1/1969 | Cox |
| 3,700,245 A | | 10/1972 | Nannini |
| 3,788,307 A | * | 1/1974 | Kistner ........................ 602/21 |
| 4,138,108 A | * | 2/1979 | Robinson ..................... 473/62 |
| 4,441,490 A | * | 4/1984 | Nirschl ........................ 602/21 |
| 4,502,688 A | | 3/1985 | Papp |
| 4,941,460 A | * | 7/1990 | Working ....................... 602/21 |
| 5,160,314 A | | 11/1992 | Peters |
| 5,324,251 A | * | 6/1994 | Watson ........................ 602/16 |
| 5,376,066 A | * | 12/1994 | Phillips et al. ................ 602/21 |
| 5,376,091 A | * | 12/1994 | Hotchkiss et al. ............. 606/55 |
| 5,456,650 A | | 10/1995 | Williams, Jr. et al. |
| 5,492,231 A | | 2/1996 | Clark |
| 5,492,331 A | * | 2/1996 | Kawakami ................... 473/213 |
| 5,499,820 A | | 3/1996 | Albertsson |
| 5,600,849 A | * | 2/1997 | Hu ................................. 2/16 |
| 5,652,955 A | * | 8/1997 | Skewis ........................... 2/20 |
| 5,653,680 A | * | 8/1997 | Cruz ............................ 602/21 |
| 5,672,150 A | * | 9/1997 | Cox ............................. 602/21 |
| 5,713,837 A | * | 2/1998 | Grim et al. .................... 602/6 |
| 5,839,124 A | * | 11/1998 | Tilton ............................ 2/170 |
| 5,848,983 A | * | 12/1998 | Basaj et al. ................... 602/22 |
| 6,199,208 B1 | | 3/2001 | Torbett |
| 6,328,706 B1 | * | 12/2001 | Yattavong .................... 602/21 |
| 6,361,447 B1 | * | 3/2002 | Lindstrom ................... 473/62 |

* cited by examiner

*Primary Examiner*—Nicholas D. Lucchesi
*Assistant Examiner*—Huong Q. Pham
(74) *Attorney, Agent, or Firm*—Edward M. Livingston (57) ABSTRACT

A wrist-angle brace has a predeterminedly resilient fingerless glove (1) with an angle brace (2). The angle brace is contour-angled as a stop-wall against which a user's wrist (8) is urged with resilience force of the fingerless glove for practicing feel of the contoured angle independently of the angle brace. The angle brace has a hand portion (9) that is extended from an arm portion (6) which is strapped onto the user's arm (7) with adjustment for arm and hand (3) size. An angle of the angle brace from the arm portion can be built in permanently for lightness of a dedicated embodiment or adjustable with an adjustable-angle brace (19) for an adjustable embodiment.

4 Claims, 8 Drawing Sheets

WRIST ANGLE BRACE

BACKGROUND OF THE INVENTION

This invention relates to wrist support at a desired angle for athletic activities that include golf, tennis, baseball, football and baseball and for medical use, such as the prevention and treatment of carpal tunnel syndrome.

There are numerous known wrist-support devices for athletic activities. Each has a slightly different way of mechanizing a body to overcome or to teach overcoming of natural wrist bending and movement. Significant achievements have been attempted with relatively subtle differences in prior art. Each attempt has been an adaptation of fastening an arm piece to a hand piece at a desired angle in order to train wrist movement for mechanization naturally. Mechanizing naturalness of wrist-movement structure, however, has remained very illusive. It appears that a major factor for success and effectiveness of the mechanization includes ease of use. It must be effort-effective for mental acceptance. For this, minor physical differences can cause major results.

The first factor in the effort-effective equation is that the present invention provides a novel wrist brace with a fingerless glove for physical effectiveness and ease of use. The glove is made of a compression type material in order to snugly fit on user's hand. The snug fit will prevent excessive bulkiness which would inhibit the user's grasp.

The second factor is that the brace of the present invention is located on the back of the user's hand. The palm area is free of any braces or straps which would impair user's ability to securely grasp items while using the brace. Similar wrist braces disclose the use of two braces, one on the palm side of the hand and one on the back side, in order to maintain the wrist at a desired angle. Others consist of adjustment straps placed in the palm area in order to maintain the hand in close proximity with the brace. Although the goal of having these devices placed in the palm area so as to maintain the desired angle of the brace is achieved, the significant defect is that users are severely restricted in their ability to grasp objects comfortably and securely while using the braces.

The final factor of the effort-effective equation is that the brace is very lightweight, about ½ an ounce. The present invention drastically reduces the weight of the brace by 1) being made of carbon graphite, a very lightweight yet sturdy material, and 2) having a reverse C-shaped curved cut-out removed from the brace to remove excess mass of the brace. Similar wrist braces are heavy, thus continually making user consciously alert to the fact that he or she is using a brace.

Combining these three factors, a glove made of a compression type material, a 'palm-free' device, and a very lightweight brace with a reverse C-shaped curved cut-out, makes the present invention distinguishable from prior similar braces.

Examples of most-closely related known but different mechanization of wrists are described in the following patent documents:

| U.S. Pat. No. | Inventor   | Issue Date  |
|---------------|------------|-------------|
| 5,499,820     | Albertsson | 03/09/1996  |
| 4,138,108     | Robinson   | 02/06/1979  |
| 5,160,314     | Peters     | 11/03/1992  |
| 3,423,095     | Cox        | 01/21/1969  |
| 5,456,650     | Williams, Jr., et al. | 10/10/1995 |
| 4,502,688     | Papp       | 03/05/1985  |
| 3,700,245     | Nannini    | 10/24/1972  |
| 5,492,331     | Kawakami   | 02/20/1996  |
| 1,469,315     | Hansard    | 10/02/1923  |
| 6,199,208     | Torbett    | 03/13/2001  |

SUMMARY OF THE INVENTION

Objects of patentable novelty and utility taught by this invention are to provide a wrist-angle brace which:

is easy to put on and take off of the wrist;

holds the wrist with sufficient pressure against an angled rigid form to provide reliable feel of the angled form and still have sufficient freedom to move for a person's sensory system to exercise feel for the angled position independently of the wrist-angle brace for effective wrist-angle training;

is form-fitting and lightly cushioned for comfort;

is simple and convenient to handle;

can be adapted to desired wrist angles; and is adaptable to arm-size and arm-height positioning.

This invention accomplishes these and other objects with a wrist-angle brace having a predeterminedly resilient fingerless glove with an aft-wrist brace. The aft-wrist brace is contour-angled as a stop-wall against which the wrist is urged with a level resilience pressure of the fingerless glove that allows the wrist to overcome the resistance pressure for practicing feel of the contoured angle independently of the wrist-angle brace. The wrist-angle brace is extended from a base portion that is strapped onto the arm with adjustment for arm and hand size. The wrist-angle brace is inserted into a pocket attached to the back side of the resilient fingerless glove so as to keep the hand in close proximity with the hand part of the brace, thereby maintaining proper hand form. A brace angle of the wrist-angle brace can be built in permanently for a dedicated embodiment or adjustable for an adjustable embodiment having an angle adjuster.

The above and other objects, features and advantages of the present invention should become even more readily apparent to those skilled in the art upon a reading of the following detailed description in conjunction with the drawings wherein there is shown and described illustrative embodiments of the invention.

BRIEF DESCRIPTION OF DRAWINGS

This invention is described by appended claims in relation to description of a preferred embodiment with reference to the following drawings which are explained briefly as follows:

DESCRIPTION OF PREFERRED EMBODIMENT

Listed numerically below with reference to the drawings are terms used to describe features of this invention. These terms and numbers assigned to them designate the same features throughout this description.

| | |
|---|---|
| 1. Fingerless glove | 17. Little-finger back side |
| 2. Angle brace | 18. Back-side fastener |
| 3. Hand | 19. Adjustable-angle brace |
| 4. Palm portion | 20. Adjustable wrist portion |
| 5. Thumb portion | 21. Flexible strap |
| 6. Arm portion | 22. Adjustment nut |
| 7. Arm | 23. Hand-side bolt |
| 8. Wrist | 24. Arm-side bolt |
| 9. Hand portion | 25. Hand boss |
| 10. Wrist portion | 26. Arm boss |
| 11. Arm strap | 27. Leaf spring |
| 12. Glove-back portion | 28. Angle-adjustment knob |
| 13. Cushioning material | 29. Knob bolt |
| 14. Thumb side | 30. Straightener rod |
| 15. Little-finger side | 31. Abutment member |
| 16. Thumb back side | 32. Fastener material |

Figure 1:
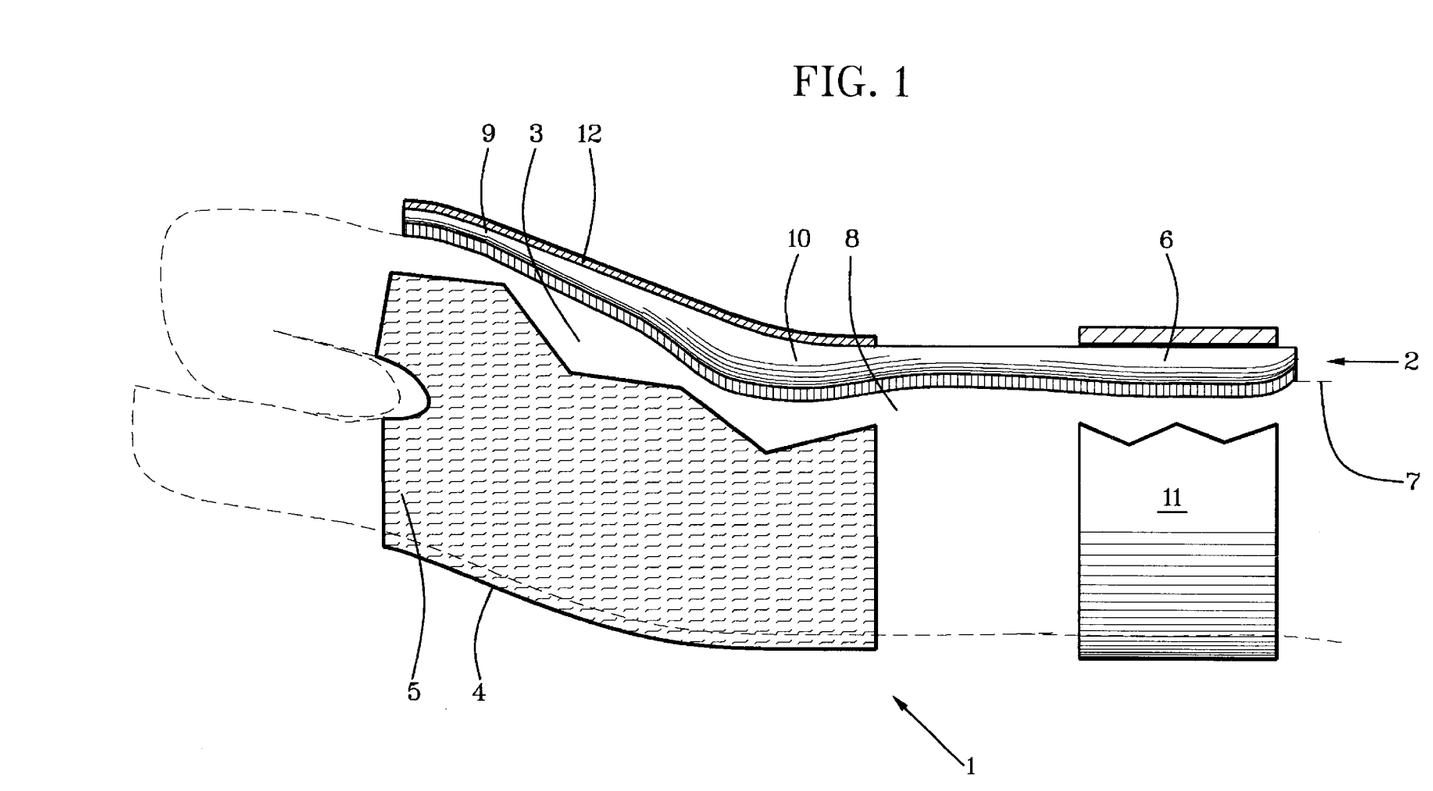
FIG. 1 is a partially cutaway side view of a wrist-angle brace having an angle brace with a fixed angle for golf-swing training positioned on a back of a hand.
Figure 2:
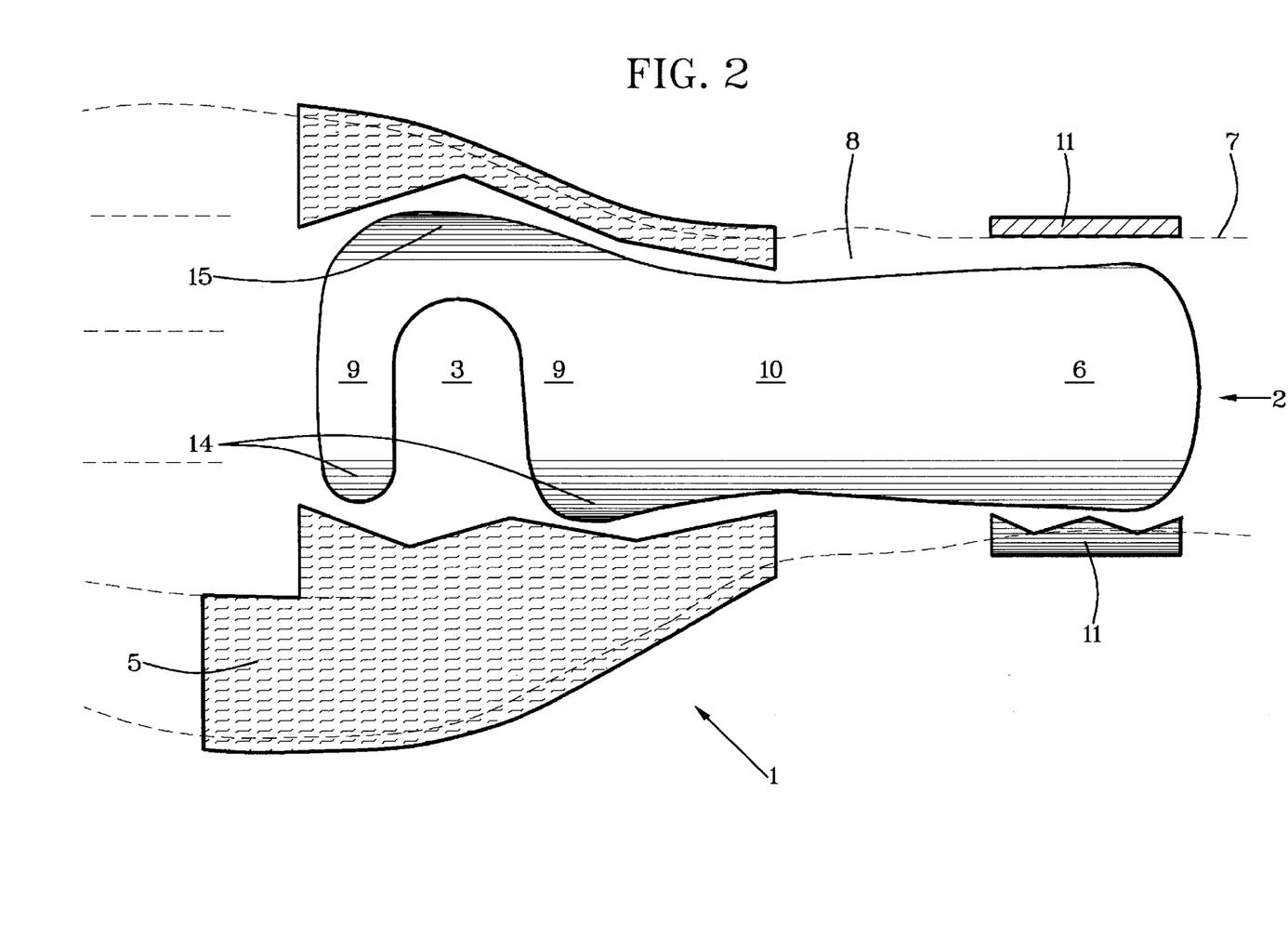
FIG. 2 is a partially cutaway top view of the wrist-angle brace illustrated in FIG. 1.
Figure 3:
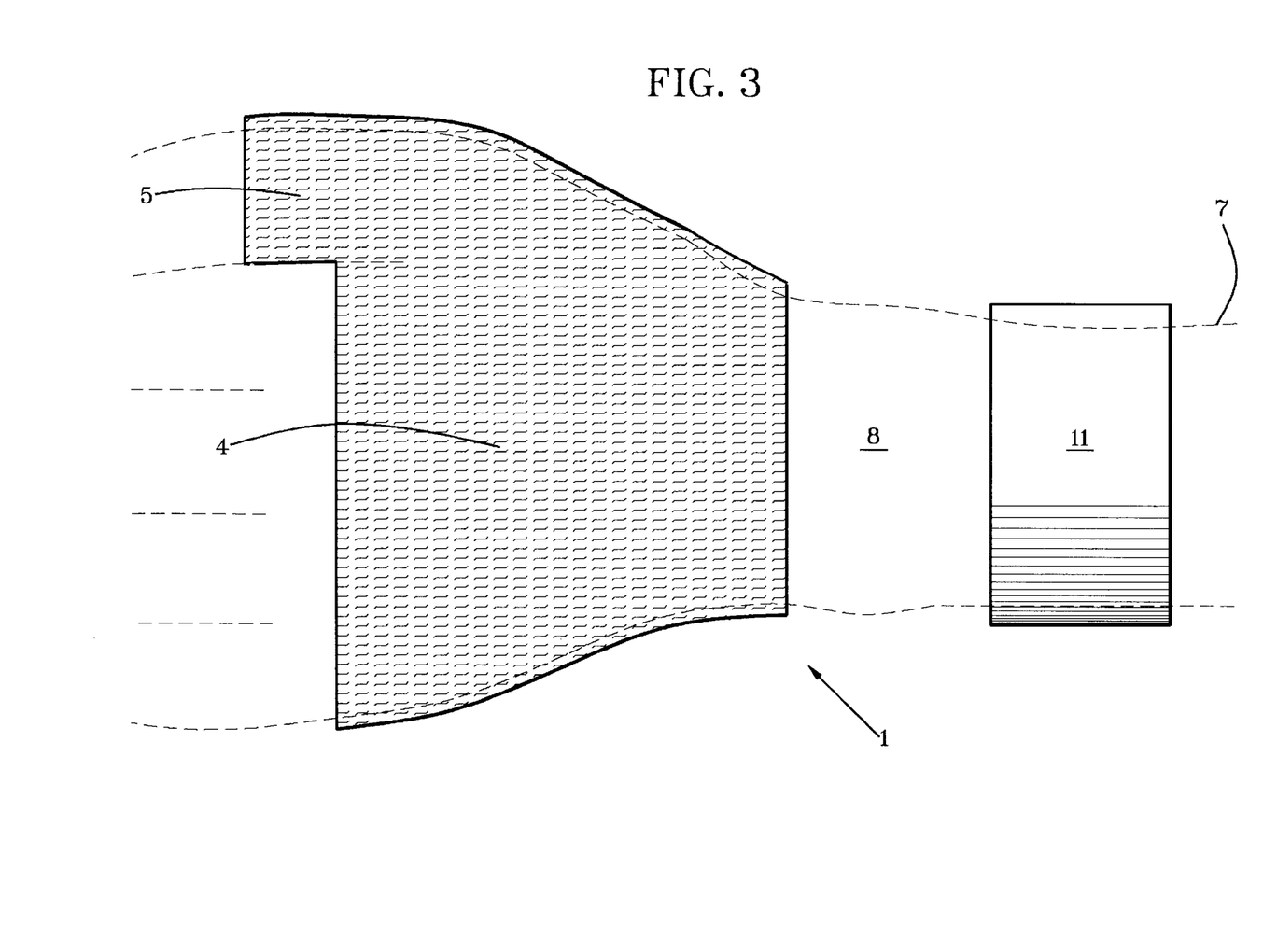
FIG. 3 is a bottom view of the wrist-angle brace illustrated in FIG. 2.

Referring to FIGS. 1–3, the wrist-angle brace has a fingerless glove 1 in which an angle brace 2 is positioned for contact with a back of a hand 3 of a user on which the fingerless glove 1 is positioned with a palm portion 4 of the fingerless glove 1 in contact with a palm of the user's hand 3 and with a thumb of the user in a thumb portion 5 of the fingerless glove 1. The angle brace 2 has an arm portion 6 that is positioned for contact with a back of the user's arm 7 upwardly on the user's arm 7 from a back of the user's wrist 8. The angle brace 2 has a hand portion 9 that is positioned for contact with a back of the user's hand 3 by insertion into a pocket either on the outside or inside of the glove 1 which is oppositely disposed from the palm of the user's hand 3. The hand portion 9 of the angle brace 2 is joined to the arm portion 6 of the angle brace 2 at a wrist portion 10 of the angle brace 2 predeterminedly at a wrist angle.

The fingerless glove 1 has contractive resilience for application of contractive force of the contractive resilience intermediate the palm of the user's hand 3 and the hand portion 9 of the angle brace 2. With an arm strap 11, the arm portion 6 of the angle brace 2 is strapped to the user's arm selectively above the user's wrist 8.

The contractive force of the contractive resilience of a glove-back portion 12 of the fingerless glove 1 on the hand portion 9 of the angle brace 2 is transmittable to the user's arm 7 through the arm portion 6 of the angle brace 2 and the arm strap 11 with the wrist portion 10 of the angle brace 2 being a fulcrum for application of leverage force of the fingerless glove 1 that is in opposition to resistance leverage from the arm strap 11 on the user's arm 7.

As shown in FIGS. 1–6, the angle brace 2 includes a fixed-angle brace with a fixed angle of the wrist portion 10 intermediate the arm portion 6 and the hand portion 9 of the angle brace 2. The wrist portion 10 of the angle brace 2 intermediate the arm portion 6 and the hand portion 9 of the angle brace 2 is predeterminedly arcuate as adapted for predetermined wrist-angle-training uses. The fixed angle can be adapted for wrist-angle training for swinging a golfclub as illustrated in FIG. 1 with the fixed angle within a range of eighteen and twenty-four degrees from a straight angle between the arm portion 6 and the hand portion 9 of the angle brace 2.

Figure 4:
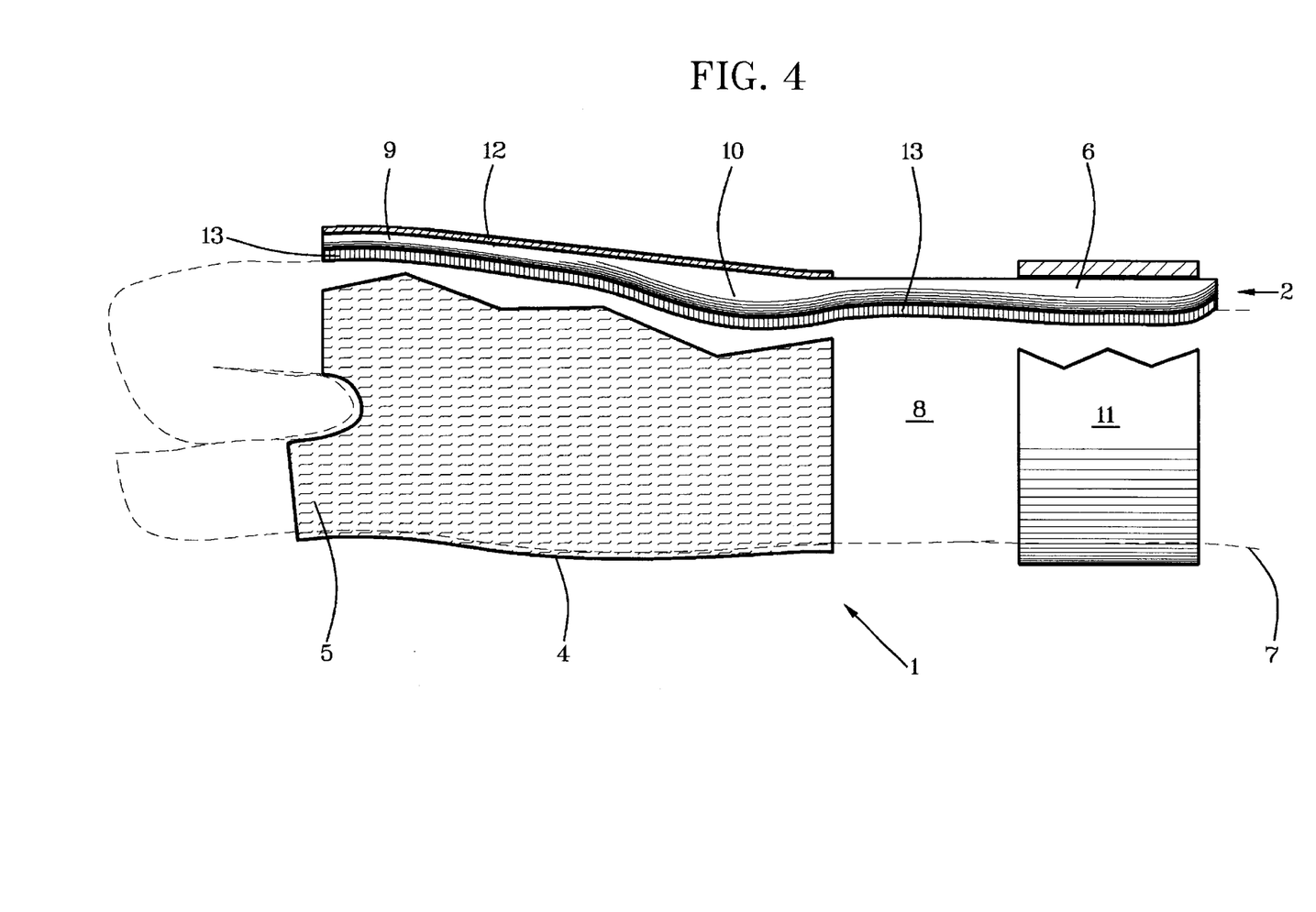
FIG. 4 is a partially cutaway side view of the wrist-angle brace in which the angle brace has a fixed angle for baseball-pitch training positioned on a back of the hand.

As illustrated in FIG. 4, the fixed angle for which the wrist-angle brace is adapted can include an angle range for wrist-angle training for various sports and other uses including pitching a baseball or for treating carpal tunnel syndrome and as a preventive measure for carpal tunnel syndrome from computer use in an office or home setting. The fixed angle for pitching a baseball is within a range of zero and four degrees from a straight angle between the arm portion 6 and the hand portion 9 of the angle brace 2. The fixed angle for carpal tunnel should fall within a range of zero to ten degrees.

Referring to FIGS. 2–6, the angle brace 2 can be adapted for direct contact with the back of the hand 3 and for being attached to the fingerless glove 1 at a finger end of the angle brace 2 proximate the hand portion 9. The angle brace 2 is made preferably of a light-weight plastic material, specifically carbon graphite, having a hand side covered with predeterminedly cushioning material 13. The hand portion 9 is a reverse C-shape so as to further promote the lightweight character of the present invention. The angle brace 2 has a width that is predeterminedly less than a width of a typical user's hand 3 and preferably includes an intentionally armfitting and hand-fitting curvature intermediate a thumb side 14 and a little-finger side 15 of the angle brace 2. The arm-fitting and hand-fitting curvature is continued predeterminedly from proximate the hand portion 9 to the arm portion 6 of the angle brace 2.

The contractive force of the contractive resilience of the fingerless glove 1 preferably is predetermined to allow bending of the user's wrist 8 away from the angle of the angle brace 2 by application of desired strength of the user in opposition to the contractive force for allowing a feel of wrist-positioning independently of the wrist-angle brace 2.

Figure 5:
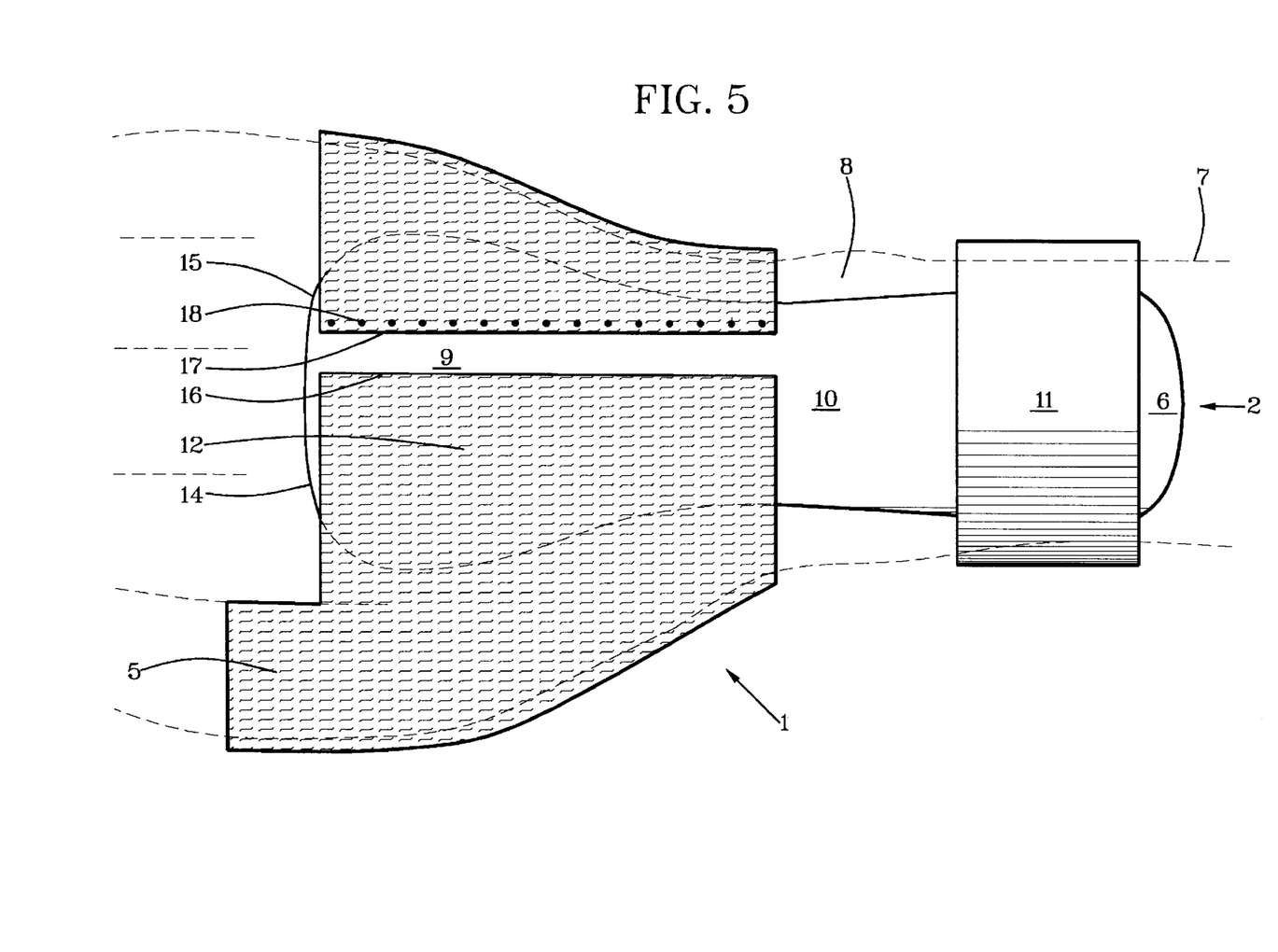
FIG. 5 is a top view of a split-back-adjustable fingerless glove with thumb-side adjustment and little-finger-side permanent attachment on a back of the hand and having an angle brace with a fixed angle.
Figure 6:
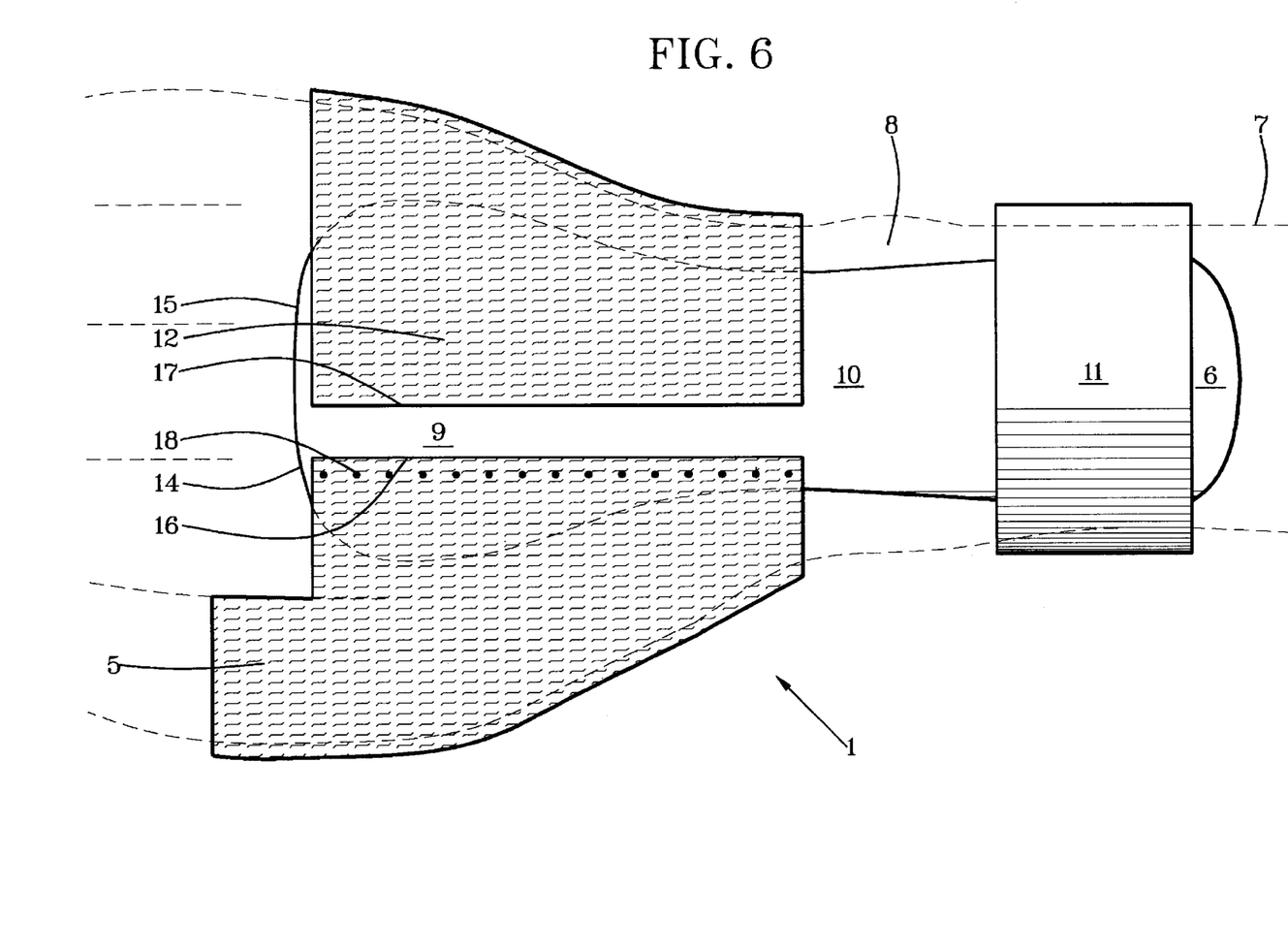
FIG. 6 is a top view of a split-back-adjustable fingerless glove with little-finger-side adjustment and thumb-side permanent attachment on a back of the hand and having the angle brace with the fixed angle.

The contractive force of the contractive resilience of the fingerless glove 1 can be adjustable to wrist 8 and hand 3 size of the user for allowing bending of the user's wrist 8 for moving the hand 3 away from the angle brace 2 by application of strength of the user selectively in opposition to the contractive force for allowing a feel of wrist-positioning independently of the wrist-angle brace. For adjustability of the contractive force of the fingerless glove 1, the fingerless glove 1 can include a split back side having an adjuster of tightness between a thumb back side 16 of the fingerless glove 1 and a little-finger back side 17 of the glove-back portion 12 of the fingerless glove 1 as shown in FIGS. 5–6. The purpose of the adjuster of tightness in this specific area is to maintain the hand 3 in close proximity to the hand portion of the wrist-angle brace 9, thus making user maintain desired form.

The adjuster of tightness can include the thumb back side 16 of the fingerless glove 1 being affixed permanently to a thumb side 14 of the back side of the angle brace 2 with one or more back-side fasteners 18 and the little-finger back side 17 of the fingerless glove 1 being length-adjustment attachable to a little-finger side 15 of the back side of the angle brace 2.

The adjuster of tightness can include the little-finger back side 17 of the fingerless glove 1 being affixed permanently to a little-finger side 15 of the back side of the angle brace 2 with one or more of the back-side fasteners 18 and the thumb back side 16 of the fingerless glove 1 being length-adjustment attachable to the thumb side 14 of the back side of the angle brace 2.

Length-adjustment attachment of either the thumb back side 16 or the little-finger back side 17 to respective sides of the angle brace 2 with hook-and-loop or other fastener means and with the opposite side being affixed permanently to the back side of the angle brace 2 also can provide a convenient means for putting the wrist-angle brace on a user's hand 3.

Figure 7:
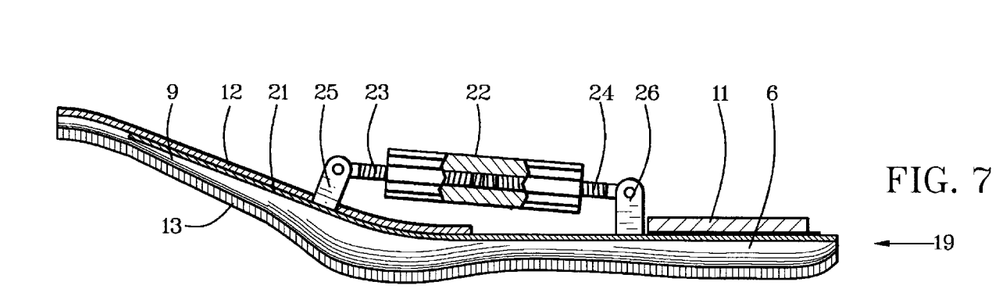
FIG. 7 is a partially cutaway side view of an angle brace having an adjustable wrist portion with a counter-threaded adjustment nut for all wrist-angle training.
Figure 8:
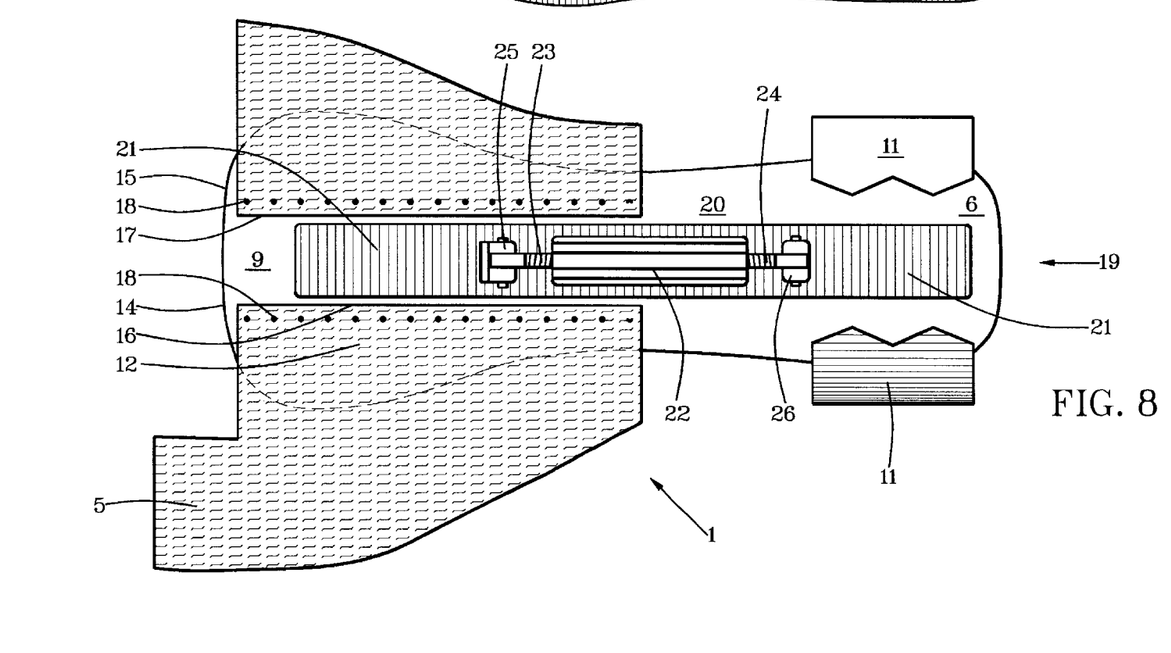
FIG. 8 is a partially cutaway top view of the FIG. 7 adjustable wrist portion in a split fingerless glove.

Referring to FIGS. 7–8, the angle brace 2 described in relation to FIGS. 1–6, can include an adjustable-angle brace 19 with an adjustable wrist portion 20 intermediate the arm portion 6 and the hand portion 9 of the adjustable-angle brace 19. The adjustable wrist portion 20 can include at least one predeterminedly flexible strap 21 intermediate the arm portion 6 and the hand portion 9 of the flexible-angle brace 19.

An angle adjuster is positioned in predetermined contact with an outside surface of the arm portion 6 and an outside surface of the hand portion 9 of the adjustable-angle brace 19 for varying angularity between the outside surface of the arm portion 6 and the outside surface of the hand portion 9 of the adjustable-angle brace 19 selectively.

As shown in FIGS. 7–8, the angle adjuster can include a counter-threaded adjustment nut 22 into which a hand-side bolt 23 is screwed into a hand end of the adjustment nut 22 and an am arm-side bolt 24 is screwed into an arm end of the adjustment nut 22. The hand-side bolt 23 is attached pivotally to a hand boss 25 and the arm-side bolt 24 is attached pivotally to an arm boss 26.

The hand-side bolt 23 and the hand end of the adjustment nut 22 are threaded in a first helical direction and the arm-side bolt 24 and the arm end of the adjustment nut 22 are threaded in a second helical direction. The adjustment nut 22 is turned in a first direction for increasing distance between the hand boss 25 and the arm boss 26 to decrease a wrist-bend angle of the adjustable-angle brace 19. The adjustment nut 22 is turned in a second direction for decreasing the distance between the hand boss 25 and the arm boss 26 to increase the wrist-bend angle of the adjustable-angle brace 19.

Figure 9:
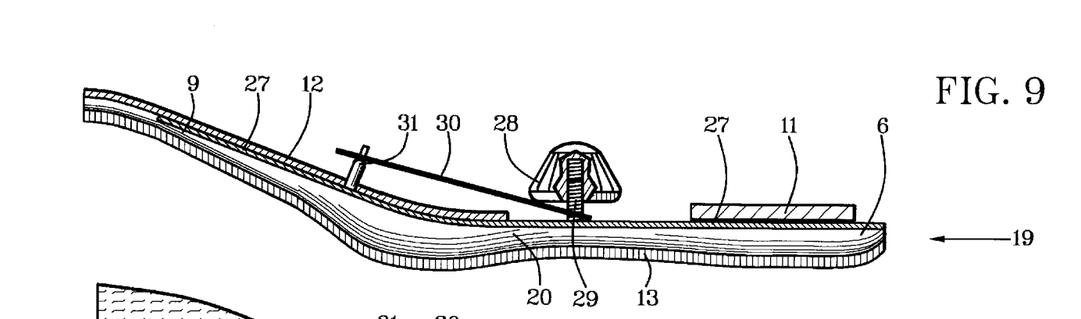
FIG. 9 is a partially cutaway side view of an angle brace having an adjustable wrist portion with an adjustment knob for all wrist-angle training.
Figure 10:
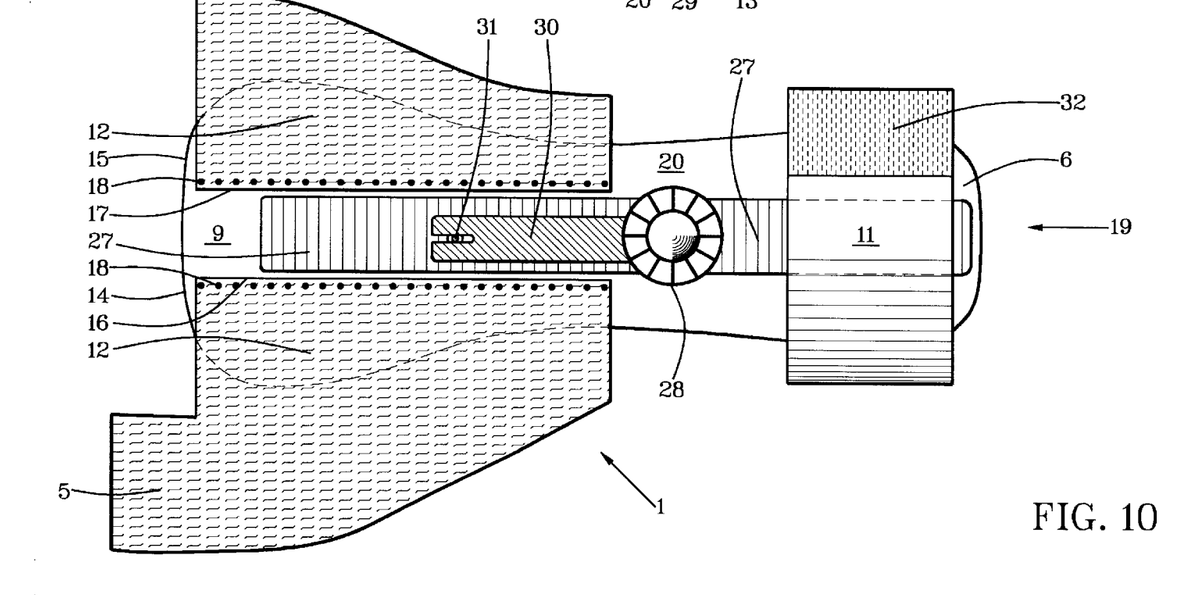
FIG. 10 is a partially cutaway top view of the FIG. 9 adjustable wrist portion in a split-back fingerless glove.

As shown in FIGS. 9–10, the flexible strap described in relation to FIGS. 7–8 can include a leaf spring 27 having a bend memory with a larger wrist-bend angle of the adjustable-angle brace 19 than desired and the angle adjuster includes a wrist-bend straightener in adjustable opposition to the bend memory of the leaf spring 27 intermediate the arm portion 6 and the hand portion 9 of the adjustable-angle brace 19. The wrist-bend straightener includes an angle-adjustment knob 28 that is screwed onto a knob bolt 29 that is extended from a back side of the arm portion 6 of the adjustable-angle brace 19.

A straightener rod 30 is anchored to the adjustable-angle brace 19 proximate the knob bolt 29. The straightener rod 30 is in contact with an abutment member 31 that is extended from a back side of the hand portion 9 of the adjustable-angle brace 19. Preferably, the straightener rod 30 includes a loose bolt orifice or a bolt bay to receive the knob bolt 29 for being anchored to the adjustable-angle brace 19. The angle-adjustment knob 28 is screwed downwardly towards the adjustable-angle brace 19 for decreasing the wrist-bend angle and upwardly for increasing the wrist bend angle.

Referring further to FIGS. 1–10, the contractive force of the contractive resilience of the fingerless glove 1 can be adjustable to wrist 8 and hand 3 size of the user for allowing bending of the user's wrist 8 to remove the user's hand away from the adjustable-angle brace 19 by application of strength of the user selectively in opposition to the contractive force for allowing a feel of wrist-positioning independently of the adjustable-angle brace 19.

The fingerless glove 1 can include a split back side having an adjuster of tightness between the thumb back side 16 of the fingerless glove 1 and the little-finger back side 17 of the fingerless glove 1. The adjuster of tightness can include the thumb back side 16 of the fingerless glove being affixed permanently to the thumb side 14 of the back side of the adjustable-angle brace 19 with the one or more back-side fasteners 18 and the little-finger back side 17 of the fingerless glove 1 being length-adjustment attachable to the little-finger side 15 of the back side of the adjustable-angle brace 19.

Optionally, the adjuster of tightness can include the little-finger back side 17 of the fingerless glove 1 being affixed permanently to the little-finger side 15 of the back side of the adjustable-angle brace 19 and the thumb back side 16 of the fingerless glove 1 being length-adjustment attachable to the thumb side 14 of the back side of the adjustable-angle brace 19.

The back-side fasteners 18 are shown on both the thumb back side 16 and the little-finger back side 17 of the fingerless glove 1 for illustrating permanent attachment to either or both sides of the adjustable-angle brace 19.

As shown in FIG. 10, the arm strap 11 can be tied with fastener material 32 that can include conventional hook-and-loop fastener material or with buckles or other belt fasteners.

A new and useful wrist-angle brace having been described, all such foreseeable modifications, adaptations, substitutions of equivalents, mathematical possibilities of combinations of parts, pluralities of parts, applications and forms thereof as described by the following claims and not precluded by prior art are included in this invention.

What is claimed is:

1. A wrist-angle brace comprising:
   a fingerless glove in which an angle brace is positioned for contact with a back of a hand of a user on which the fingerless glove is positioned with a palm portion of the fingerless glove in contact with a palm of the user's hand and with a thumb of the user in a thumb portion of the fingerless glove;
   a substantially rigid angle brace of lightweight plastic material adapted to conform to a top surface of a hand, wrist and lower portion of a forearm when the wrist is flexed upwardly wherein said angle brace has a forearm portion and a hand portion;
   the hand portion of the angle brace being joined to the forearm portion of the angle brace at a wrist portion of the angle brace predeterminedly at a wrist angle;
   said fingerless glove having a contractive resilience located along the palm of the user's hand for application of a contractive force;

an arm strap with which the forearm portion of the angle brace is strapped to the user's arm selectively above the user's wrist;

said fingerless glove is adjustable to wrist and hand size of the user;

an adjuster of tightness between a thumb back side of said fingerless glove and a little-finger back side of said fingerless glove wherein said adjuster of tightness includes said thumb back side of the fingerless glove being affixed permanently to a thumb side of the back side of the angle brace with one or more back-side fasteners and the little-finger back side of the fingerless glove being length-adjustment attachable to a little-finger side of the back side of the angle brace;

an angle adjuster positioned in predetermined contact with an outside surface of said forearm portion and an outside surface of said hand portion;

said angle adjuster having a wrist-bend straightener; and said angle brace having a reverse C-shaped curved cut-out on said hand portion.

2. A wrist-angle brace comprising:

a fingerless glove in which an angle brace is positioned for contact with a back of a hand of a user on which the fingerless glove is positioned with a palm portion of the fingerless glove in contact with a palm of the user's hand and with a thumb of the user in a thumb portion of the fingerless glove;

a substantially rigid angle brace of lightweight plastic material adapted to conform to a top surface of a hand, wrist and lower portion of a forearm when the wrist is flexed upwardly wherein said angle brace has a forearm portion and a hand portion;

the hand portion of the angle brace being joined to the forearm portion of the angle brace at a wrist portion of the angle brace predeterminedly at a wrist angle;

said fingerless glove having a contractive resilience located along the palm of the user's hand for application of a contractive force;

an arm strap with which the forearm portion of the angle brace is strapped to the user's arm selectively above the user's wrist;

said fingerless glove is adjustable to wrist and hand size of the user;

an adjuster of tightness between a thumb back side of said fingerless glove and a little-finger back side of said fingerless glove wherein said adjuster of tightness includes the little-finger side of the fingerless glove being affixed permanently to a little-finger side of the back side of the angle brace with one or more back-side fasteners and the thumb side of the fingerless glove being length-adjustment attachable to the thumb side of the back side of the angle brace;

an angle adjuster positioned in predetermined contact with an outside surface of said forearm portion and an outside surface of said hand portion;

said angle adjuster having a wrist-bend straightener; and said angle brace having a reverse C-shaped curved cut-out on said hand portion.

3. A wrist-angle brace comprising:

a fingerless glove in which an angle brace is positioned for contact with a back of a hand of a user on which the fingerless glove is positioned with a palm portion of the fingerless glove in contact with a palm of the user's hand and with a thumb of the user in a thumb portion of the fingerless glove;

a substantially rigid angle brace of lightweight plastic material adapted to conform to a top surface of a hand, wrist and lower portion of a forearm when the wrist is flexed upwardly wherein said angle brace has a forearm portion and a hand portion;

the hand portion of the angle brace being joined to the forearm portion of the angle brace at a wrist portion of the angle brace predeterminedly at a wrist angle;

said fingerless glove having a contractive resilience located along the palm of the user's hand for application of a contractive force;

an arm strap with which the forearm portion of the angle brace is strapped to the user's arm selectively above the user's wrist;

said fingerless glove is adjustable to wrist and hand size of the user;

an adjuster of tightness between a thumb back side of said fingerless glove and a little-finger back side of said fingerless glove;

an angle adjuster positioned in predetermined contact with an outside surface of said forearm portion and an outside surface of said hand portion wherein said angle adjuster includes a counter-threaded adjustment nut into which a hand-side bolt is screwed into a hand end of the adjustment nut and an arm-side bolt is screwed into an arm end of the adjustment nut;

said hand-side bolt is attached pivotally to a hand boss and the arm-side bolt is attached pivotally to an arm boss;

said hand-side bolt and the hand end of the adjustment nut are threaded in a first helical direction and the arm-side bolt and the arm end of the adjustment nut are threaded in a second helical direction;

said adjustment nut is turned in a first direction for increasing distance between the hand boss and the arm boss to decrease a wrist-bend angle of the angle brace;

said adjustment nut is turned in a second direction for decreasing the distance between the hand boss and the arm boss to increase the wrist-bend angle of the angle brace;

said angle adjuster having a wrist-bend straightener; and said angle brace having a reverse C-shaped curved cut-out on said hand portion.

4. A wrist-angle brace comprising:

a fingerless glove in which an angle brace is positioned for contact with a back of a hand of a user on which the fingerless glove is positioned with a palm portion of the fingerless glove in contact with a palm of the user's hand and with a thumb of the user in a thumb portion of the fingerless glove;

a substantially rigid angle brace of lightweight plastic material adapted to conform to a top surface of a hand, wrist and lower portion of a forearm when the wrist is flexed upwardly wherein said angle brace has a forearm portion and a hand portion;

the hand portion of the angle brace being joined to the forearm portion of the, angle brace at a wrist portion of the angle brace predeterminedly at a wrist angle;

said fingerless glove having a contractive resilience located along the palm of the user's hand for application of a contractive force;

an arm strap with which the forearm portion of the angle brace is strapped to the user's arm selectively above the user's wrist;

said fingerless glove is adjustable to wrist and hand size of the user;

an adjuster of tightness between a thumb back side of said fingerless glove and a little-finger back side of said fingerless glove;

an angle adjuster positioned in predetermined contact with an outside surface of said forearm portion and an outside surface of said hand portion;

said angle adjuster having a wrist-bend straightener wherein said wrist-bend straightener includes an angle-adjustment knob that is screwed onto a knob bolt that is extended from a back side of the arm portion of the angle brace;

a straightener rod is anchored to the angle brace proximate the knob bolt;

said straightener rod is in contact with an abutment member that is extended from a back side of the hand portion of the angle brace for decreasing the wrist-bend angle and upwardly for increasing the wrist-bend angle;

said adjustment knob is screwed downwardly towards the angle brace; and said angle brace having a reverse C-shaped curved cut-out on said hand portion.

* * * * *